(12) United States Patent
Markovic

(10) Patent No.: US 8,530,428 B2
(45) Date of Patent: Sep. 10, 2013

(54) TREATING CANCER WITH GRANULOCYTE-MACROPHAGE COLONY STIMULATING FACTOR

(75) Inventor: Svetomir N. Markovic, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 336 days.

(21) Appl. No.: 12/529,897

(22) PCT Filed: Mar. 7, 2008

(86) PCT No.: PCT/US2008/056209
§ 371 (c)(1),
(2), (4) Date: Apr. 26, 2011

(87) PCT Pub. No.: WO2008/109818
PCT Pub. Date: Sep. 12, 2008

(65) Prior Publication Data
US 2011/0190219 A1 Aug. 4, 2011

Related U.S. Application Data

(60) Provisional application No. 60/893,429, filed on Mar. 7, 2007.

(51) Int. Cl.
*A61K 38/14* (2006.01)
*A61K 9/12* (2006.01)

(52) U.S. Cl.
USPC ........ 514/19.2; 514/19.3; 514/19.8; 514/21.1

(58) Field of Classification Search
None
See application file for complete search history.

(56) References Cited

U.S. PATENT DOCUMENTS 5,078,996 A 1/1992 Conlon, III et al.
5,904,920 A 5/1999 Dranoff et al.

OTHER PUBLICATIONS

Lin, 2010, Current Hematologic Malignancy Reports, vol. 5, pp. 29-34.*
Wylam, 2006, European Respiratory Journal, vol. 27, pp. 585-593.*
Borrello and Pardoll, "GM-CSF-based cellular vaccines: a review of the clinical experience," *Cytokine & Growth Factor Reviews*, 2002, 13: 185-193.
Anderson et al., "Aerosol Granulocyte Macrophage-Colony Stimulating Factor: A Low Toxicity, Lung-specific Biological Therapy in Patients with Lung Metastases," *Clin. Cancer Res.*, 1999, 5:2316-2323.
Armitage, "Emerging Applications of Recombinant Human Granulocyte-Macrophage Colony-Stimulating Factor," *Blood*, 1998, 92(12):4491-4508.
Binet et al., "Synergistic action of alkylating agents and methylxanthine derivatives in the treatment of chronic lymphocytic leukemia," *Leukemia*, 1995, 9(12):2159-2162.
Bunn et al., "Chemoradiotherapy With or Without Granulocyte-Macrophage Colony-Stimulating Factor in the Treatment of Limited-Stage Small-Cell Lung Cancer: A Prospective Phase III Randomized Study of the Southwest Oncology Group," *J. Clin. Oncol.*, 1995, 13(7):1632-1641.
Dighiero et al., "Chlorambucil in Indolent Chronic Lymphocytic Leukemia," *New Engl. J. Med.*, 1998, 338(21):1506-1514.
Dorr, "Clinical Properties of Yeast-Derived Versus *Escherichia coli*-Derived Granulocyte-Macrophage Colony-Stimulating Factor," *Clin. Ther.*, 1993, 15:19-29.
Dranoff et al., "Vaccination with irradiated tumor cells engineered to secrete murine granulocyte-macrophage colony-stimulating factor stimulates potent, specific, and long-lasting anti-tumor immunity," *Proc. Natl. Acad. Sci. USA*, 1993, 90:3539-3543.
Edmonson et al., "Cytotoxic Drugs Plus Subcutaneous Granulocyte-Macrophage Colony-Stimulating Factor: Can Molgramostim Enhance Antisarcoma Therapy?" *J. Nat. Cancer Inst.*, 1994, 86(4):312-314.
Edmonson, "Chemotherapeutic Approaches to Soft Tissue Sarcomas," *Sem. Surg. Oncol.*, 1994, 10:357-363.
Edmonson, "Needed: Qualitative Improvement in Antisarcoma Therapy," *J. Clin. Oncol.*, 1995, 13(7):1531-1533.
Edmonson et al., "Can molgramostim enhance the antitumor effects of cytotoxic drugs in patients with advanced sarcomas?" *Ann. Oncol.*, 1997, 8:637-641.
Liang and Zeger, "Longitudinal data analysis using generalized linear models," *Biometrika*, 1986, 73:13-22.
McCullagh and Nelder, Generalized Linear Models, Second Edition, 1989, Chapman and Hall, London, 6 pages.
Perkins et al., "Effects of Continuous High Dose rhGM-CSF Infusion on Human Monocyte Activity," *Am. J. Hematol.*, 1993, 43:279-285.
Rao et al., "Aerolized granulocyte macrophage-colony stimulating factor(GM-CSF) therapy in metastic cancer," *Am. J. Clin. Oncol.*, 2003, 26(5):493-498.
Rose et al., "The Effect of Aerosolized Recombinant Human Granulocyte Macrophage Colony-stimulating Factor or Lung Leukocytes in Nonhuman Primates," *Am. Rev. Respir. Dis.*, 1992, 146:1279-1286.
Rowe et al., "A Randomized Placebo-Controlled Phase III Study of Granulocyte-Macrophage Colony-Stimulating Factor in Adult Patients (>55 to 70 Years of Age) With Acute Myelogenous Leukemia: A Study of the Eastern Cooperative Oncology Group (E1490)," *Blood*, 1995, 86(2):457-462.

(Continued)

*Primary Examiner* — Joanne Hama
*Assistant Examiner* — Ian Dang
(74) *Attorney, Agent, or Firm* — Fish & Richardson P.C.

(57) ABSTRACT

Methods for treating cancer (e.g., metastatic cancer to the lung or chronic lymphocytic leukemia) in patients are described that include administrating an aerosolized granulocyte macrophage colony stimulating factor to the patients. Methods for stimulating an immune response in patients also are described.

9 Claims, No Drawings

(56) References Cited

OTHER PUBLICATIONS

Steward et al., "Effects of Granulocyte-Macrophage Colony-Stimulating Factor and Dose Intensification of V-ICE Chemotherapy in Small-Cell Lung Cancer: A Prospective Randomized Study of 300 Patients," *J. Clin. Oncol.*, 1998, 16(2):642-650.

Witz et al., "A Placebo-Controlled Study of Recombinant Human Granulocyte-Macrophage Colony-Stimulating Factor Administered During and After Induction Treatment for De Novo Acute Myelogenous Leukemia in Elderly Patients," *Blood*, 1998, 91(8):2722-2730.

Authorized Officer Yun-Kyung Kim, International Search Report and Written Opinion of the International Searching Authority, PCT/US2008/056209, mailed Aug. 1, 2008, 9 pages.

Authorized Officer Ellen Moyse, International Preliminary Report on Patentability, PCT/US2008/056209, mailed Sep. 8, 2009, 7 pages.

\* cited by examiner

US 8,530,428 B2

TREATING CANCER WITH GRANULOCYTE-MACROPHAGE COLONY STIMULATING FACTOR

CROSS-REFERENCE TO RELATED APPLICATIONS

This application is a National Stage application under 35 U.S.C. §371 and claims benefit under 35 U.S.C. §119(a) of International Application No. PCT/US2008/056209, having an International Filing Date of Mar. 7, 2008, which claims the benefit of U.S. Provisional Application Ser. No. 60/893,429, filed Mar. 7, 2007. The disclosures of the prior applications are considered part of (and are incorporated by reference in) the disclosure of this application.

TECHNICAL FIELD

This disclosure relates to the use of aerosolized granulocyte-macrophage colony stimulating factor (GMCSF) to treat cancer (e.g., metastatic cancers to the lung and leukemia) in humans, and to stimulate an immune response in immunocompromised humans.

BACKGROUND

GMCSF is a glycoprotein with a molecular weight of approximately 22 kD and is encoded by a gene on chromosome 5q31. GMCSF is produced by many cells of the body, including T cells, macrophages, mast cells, endothelial cells, and fibroblasts. Receptors for GMCSF polypeptides are found on both hematopoietic cells and non-hematopoietic cells and on some tumor cell lines. GMCSF receptors can be heterodimers composed of a ligand-binding α-chain and a β-chain that allows for high-affinity binding and signal transduction. The α-chain can uniquely bind GMCSF, but the β-chain also can be utilized by receptors for IL-3 and IL-5. GMCSF can exert its action locally as a potent growth factor, stimulating the proliferation and maturation of primitive hematopoietic progenitor cells (CFU-GEMM), megakaryocytic progenitor cells, as well as erythroid progenitor cells. It also can stimulate functional activities of many neutrophils, monocytes, macrophages, and dendritic cell functions, enhancing their ability to respond to secondary triggering mechanisms.

SUMMARY

This disclosure relates to methods and materials for using a GMCSF to treat metastatic cancer to the lung and leukemia (e.g., chronic lymphocytic leukemia). As described herein, aerosol delivery of a GMCSF can allow for delivery to the lung, resulting in an effective treatment of metastatic cancer to the lung, while minimizing hematopoietic effects on peripheral white blood cells. A GMCSF delivered to the lung by aerosol can be absorbed by bronchial and pulmonary lymphatics, drain to pulmonary and mediastinal lymph nodes, and finally enter the circulation via the thoracic duct. Without being bound by any particular mechanism, if immune cells with high-affinity receptors are present in lymphatics or lymph nodes in the chest, absorbed GMCSF may be stopped within the chest and activate cells within the thorax but not the circulation. In other words, aerosol delivery of a GMCSF to the lung can provide a significant dose to immune cells within the lung, but little systemically.

In one aspect, a method for treating metastatic cancer to the lung in a human is provided. The method includes administering to a lung of the human, between 1.5 and 10 mg of a GMCSF in a 24 hour period. In some cases, between 750 μg and 5 mg of a GMCSF can be administered in a 12 hour period. When administered, the GMCSF may be administered in a dose of between 750 μg and 5 mg. In certain cases, the GMCSF may be administered in a dose of between 1 mg and 2.5 mg, or in some cases, a dose of 2 mg.

A GMCSF can be administered for seven days, followed by seven days of no administration. GMCSF can be administered in the form of an aerosol, and can be administered, at most, twice daily to the human. The cancer that metastasized to the lung can be a renal cell carcinoma, leiomyosarcoma, Ewing's sarcoma, osteosarcoma, or melanoma.

Also provided herein is a method for treating chronic lymphocytic leukemia in a human. The method includes administering to a lung of the human, between 1.5 and 10 mg of GMCSF polypeptide in a 24 hour period. A GMCSF can be administered in the form of an aerosol.

In another aspect, the disclosure features a method for inducing an immune response in a human. The method includes co-administering a GMCSF and an antigen to the human in an effective amount to stimulate the immune response. In some embodiments, the GMCSF and antigen can induce an immune response both systemically and mucosally. The GMCSF can be administered to the human in an amount between 1.5 and 10 mg in a 24 hour period. The GMCSF can be administered in the form of an aerosol. The GMCSF and antigen aerosol can be administered nasally. The antigen can be a tumor or microbial antigen (e.g., a vaccine composition).

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

This disclosure provides methods and materials for treating metastatic cancer to the lung of a human and for treating leukemia (e.g., chronic lymphocytic leukemia; CLL) in a human. As used herein, "treatment of metastatic cancer to the lung" refers to slowing of tumor growth, stopping tumor growth, a reduction in tumor size, or disappearance of tumor. Non-limiting examples of cancers that metastasize to the lung include renal cell carcinoma, leiomyosarcoma, Ewing's sarcoma, osteosarcoma, melanoma, fibrosarcoma, synovial cell sarcoma, and hemangiopericytoma.

As used herein, "treatment of CLL" refers to a decrease in number of circulating lymphocytes and/or regression of adenopathy or hepatosplenomegaly. Chronic lymphoid malignancies result from a clonal expansion of mature lymphocytes, and include B cell chronic lymphocytic leukemia (B-CLL), T-CLL, hairy cell disease, prolymphocytic leukemias, small cleaved cell leukemia, Sezary syndrome, adult T cell lymphoma-leukemia, and large granular lymphocyte leukemia. In the Western Hemisphere, B-CLL is the most predominant form of leukemia and accounts for about 25-30% of all leukemias. In the United States, the approximate overall annual incidence is 2.7 cases per 100,000 persons, and in humans over 60 years of age, it is greater than 20 per 100,000 persons. An estimated 10,000 new cases are diagnosed each year with a median age at diagnosis of 55 to 60 years with a 2:1 male to female ratio. Many of these humans are diagnosed incidentally during routine blood work with the finding of an elevated white count, an absolute lymphocyte count greater than 5,000/mL.

In some cases, a method provided herein for treating cancer can include administering a GMCSF to a human in an amount from about 1.5 mg to about 10 mg (e.g., from about 1.5 to about 9 mg, from about 1.5 to about 8 mg, from about 1.5 to about 7 mg, from about 2 to about 10 mg, from about 2.5 to about 10 mg, from about 3 to about 10 mg, from about 4 to about 10 mg, from about 2 to about 9 mg, or from about 2 to about 8 mg) in a 24 hour period. In some cases, a GMCSF can be administered in an amount from about 750 µg to about 5 mg (e.g., from about 750 µg to about 5 mg, from about 750 µg to about 4.5 mg, from about 750 µg to about 4 mg, from about 750 µg to about 3.5 mg, from about 1 to about 5 mg, from about 1.5 to about 5 mg, 2 to about 5 mg, from about 1 to about 4 mg, or from about 1 to about 3 mg) in a 12 hour period. In some cases, a GMCSF can be administered in an amount from about 750 µg to about 5 mg (e.g., from about 750 µg to about 5 mg, from about 750 µg to about 4.5 mg, from about 750 µg to about 4 mg, from about 750 µg to about 3.5 mg, from about 1 to about 5 mg, from about 1.5 to about 5 mg, from about 2 to about 5 mg, from about 1 to about 4 mg, or from about 1 to about 3 mg) per dose. For example, a dose of a GMCSF polypeptide can be from 1 mg to 2.5 mg, or, in certain instances, a dose can be 2 mg of a GMCSF.

A GMCSF can be administered in the form of an aerosol and can be administered one or more times (e.g., one, two, three, four, five, six, seven, eight, nine, ten, or more times) a day to a human. Administration can occur at various intervals throughout the day (e.g., every 12 hours, every 11 hours, every 10 hours, every 9 hours, at 13 hours and 20 hours, at 14 hours and 21 hours, at 13 hours and 22 hours, and at 10 hours and 24 hours). In some cases, the human is administered a GMCSF twice daily (BID) for seven days (e.g., 2 mg BID) followed by seven days of rest from GMCSF before repeating. In some cases, the human is administered a GMCSF for four to 14 days (e.g., 4 to 14 days, 4 to 13 days, 4 to 12 days, 4 to 10 days, 5 to 14 days, 6 to 14 days, 7 to 14 days, 5 to 12 days, 6 to 11 days, and 7 to 10 days), followed by an interval of rest of 4 to 14 days (e.g., 4 to 14 days, 4 to 13 days, 4 to 12 days, 4 to 10 days, 5 to 14 days, 6 to 14 days, 7 to 14 days, 5 to 12 days, 6 to 11 days, and 7 to 10 days). In some cases, treatment cycles may be repeated one or more times (e.g., repeated one, two, three, four, five, or more times).

In some embodiments, administration of GMCSF as described herein can increase the amount of cytotoxic T lymphocytes (CTLs) in a human when compared to a human not administered GMCSF as described herein. In some embodiments, the amount of CTL is as measured in the peripheral blood. In some embodiments, the CTLs are tetramer positive CTLs. In some embodiments, the tetramer positive CTLs are antigenic to one or more of gp100, MART-1, and tyrosinase. In some embodiments, the tetramer positive CTLs are antigenic to gp100. The amount of CTL can be measured using the tetramer assay for HLA-A2 cognant melanoma differentiation antigen specific peptides (e.g., MART-1$_{27-35}$, gp100$_{209-217}$, and tyrosinase$_{368-376}$).

A GMCSF can be obtained commercially, for example, as Sargramostim (Leukine™) from Immunex (Seattle, Wash.). Leukine™ is glycosylated and is derived from yeast. In some cases, a GMCSF can be produced recombinantly using standard technology. E. coli derived GMCSF can be non-glycosylated.

Aerosol delivery can be used to provide a means for achieving local effects in the lung with minimal systemic drug exposure. For example, a GMCSF can be nebulized by adding the appropriate dose of GMCSF to a nebulizer with a saline solution, such as Bronchosaline from Blalrex Laboratories, Columbus, Ohio. An aerosol mist can be produced using an air compressor. Commercially available nebulizers are efficient and deposit 3-9% of output into the mouth, 5-10% into conductive nonrespiratory bronchi (generations 0-16), and 12-20% into bronchial generations 17-23, the transitory zones of airways leading to terminal alveolated lung. Thus, ~15-20% of the aerosolized polypeptide can be delivered specifically to the lung with each dose.

This disclosure also provides methods for stimulating an immune response in a mammal (e.g., a human) by, for example, co-administering a GMCSF and an antigen (e.g., a vaccine composition). Examples of antigens that can be used include vaccines such as vaccines against *Hemophilus influenzae*, *Streptococcus pneumoniae*, or other pathogens, as well as tumor antigens. The antigens can be polypeptides that encode a full-length polypeptide or a fragment thereof.

EXAMPLES

Example 1

Method of Treating Metastatic Melanoma

The following was performed to determine whether or not dose escalation of aero-GMCSF is safe, results in further increase of melanoma specific CTLs, and affects clinical outcomes.

A 5+5 dose escalation clinical trial was conducted to determine the dose of aero-GMCSF that would increase the frequency of peripheral blood melanoma specific CTLs in HLA-A2+ patients with metastatic melanoma to the lungs. Aero-GMCSF was administered twice daily on days 1 to 7 and 15 to 21 of a 28 day cycle at doses of: 500 μg, 750 μg, 1 mg, 1.25 mg, 1.5 mg, 1.75 mg, and 2 mg per cohort.

If at most two of the first five patients at a dose level reported a 5-fold increase in CTLs, dose escalation occurred. If not, five additional patients were treated at that dose. Dose escalation continued until at least seven of the ten patients treated at a given dose level reported a 5-fold increase in CTLs or all dose levels were exhausted. Likewise, enrollment was to be suspended if ≧two of five patients enrolled onto a dose level developed severe toxicity.

The study accrued 40 patients over a period of four years. Four patients cancelled participation prior to receiving treatment. One patient was found to be ineligible du to inadequate $FEV_1$ levels. One patient was replaced (500 μg) as he died of rapid progression of disease within 13 days of registration. Among the 34 remaining patients, the median age was 58 (23-84), 72% were male, and 72% had a PS=0 (see Table 1). Dose escalation was not terminated due to excessive toxicity.

TABLE 1

Patient characteristics at study entry

| | Dose of GM-CSF per cohort | | | | | | |
|---|---|---|---|---|---|---|---|
| Characteristics | 500 µg (n = 5) | 750 µg (n = 5) | 1 mg (n = 5) | 1.25 mg (n = 5) | 1.5 mg (n = 3) | 1.75 mg (n = 5) | 2.0 mg (n = 6) |
| Male | 80% | 80% | 80% | 60% | 100% | 60% | 60% |
| Median age | 48 | 55 | 56 | 60 | 80 | 72 | 56 |
| (range) | (37-78) | (23-74) | (48-77) | (52-67) | (61-84) | (57-84) | (38-79) |
| ECOG PS | | | | | | | |
| 0 | 80% | 100% | 40% | 100% | 67% | 40% | 83% |
| 1 | 20% | 0% | 60% | 0% | 33% | 60% | 17% |
| Prior Radiation Therapy | 40% | 20% | 40% | 20% | 0% | 40% | 33% |
| Prior systemic therapy | 60% | 80% | 60% | 60% | 33% | 60% | 50% |
| Metastatic sites other than lung (M1c) | 80% | 40% | 20% | 100% | 33% | 60% | 50% |

Yeast derived, glycosylated recombinant GMCSF (Sargramostim/Leukine, Berlex Labs, Settle Wash.) was provided by the manufacturer. Each vial contained powdered GMCSF that was reconstituted with sterile or bacteriostatic water for injection, per package insert. Patients were instructed on dose preparation prior to the first cycle of therapy.

Reconstituted GMCSF (with sterile or bacteriostatic water) was added into a nebulizer bowl of a PAR LC PLUS nebulizer connected to a standard air compressor to generate the aerosol mist (Pulmo-Aide; DeVilbiss). When necessary (at the low dose range) Bronchosaline (Blalrex labs, Columbus, Ohio) was added to the nebulizer bowl to bring up the volume of the GMCSF to 2 mL (minimal volume for nebulization). Patients inhaled the mist through a valved mouthpiece provided with the nebulizer kit. Aerosol treatments were typically completed in 5-15 min. The first aerosol GMCSF treatment was observed in the clinic to be certain that maximal aerosol drug delivery is achieved. All subsequent treatments were self administered.

Each patient underwent a peripheral blood collection, tumor burden assessment (RECIST) and toxicity evaluation using the NCI-CTC version 2.0 criteria prior to the first two cycles of treatment and every other cycle thereafter until treatment was discontinued. Patients who developed moderate dyspnea (grade 3) had to hold further study treatment until symptoms improved to $\leq$ grade 2 and reduce GMCSF dose by 50% for subsequent treatments. If symptoms did not improve within 2 weeks, treatment was discontinued. Patients who developed a grade 4 dyspnea immediately discontinued treatment.

Upon completion of sample collection for a given patients, all specimens (peripheral blood mononuclear cells) were batch analyzed for surface expression of the following CD antigens: CD3, CD4, CD8, CD11c, CD14, CD16, CD20, CD22, CD32, CD44, CD45, CD56, CD62, CD69, HLA-DR, CD80, CD83, CD86, and CD123. The stained cells were washed and fixed with 2% paraformaldehyde. Flow-cytometric analysis was performed using a FACSCalibur flow cytometer and analyzed by Cellquest (Becton-Dickinson, Franklin Lakes, N.J.). Inter assay variability demonstrates a coefficient of variation (CV) of <10%.

For tetramer analysis of tumor antigen specific cytotoxic T lymphocytes (CTL), thawed PBMCs were stained with FITC conjugated anti-CD8, PC5 conjugated anti-human CD4, CD14 and CD19 and PE labeled HLA-A2 tetramers containing melanoma specific differentiation antigen peptides MART-$1_{27-35}$, gp100$_{209-217}$ or tyrosinase$_{368-376}$ (Beckman Coulter, Fullerton Calif.). Samples were analyzed by flow-cytometry and data was processed using Cellquest® software (Becton-Dickinson, Franklin Lakes, N.J.). Gates were set on lymphocytes that were CD4, CD14 and CD19 (PC5) negative. Immunophenotyping of lymphocyte subsets (CD3, CD4, CD8, CD20, CD22, and CD14) was performed using FITC or PE labeled monoclonal antibodies in accordance to manufacturer's instructions (Becton-Dickinson, Franklin Lakes, N.J.). Samples were analyzed by flow-cytometry using the same software as described above. Inter assay CV was consistently <10% for all tetramers.

Toxicities $\leq$ grade 2 (at least probably treatment related) included: grade 2 cough (1) and grade 2 rash (1) at 750 µg; grade 2 dyspnea (1) and grade 2 fatigue (1) at 1 mg; grade 2 constipation (1) at 1.5 mg; grade 2 fatigue (1), grade 3 cough (1), and grade 4 dyspnea (1) at 1.75 mg; and grade 2 dizziness (1) and grade 2 nausea (1) at 2 mg. The dose resulting in the most patients exhibiting at least 2-fold increase in melanoma differentiation antigen specific CTLs by tetramer assay was 2 mg (4 of 5 patients).

With regard to clinical benefit, one patient enrolled at the 2000 ug dose level continues to receive study treatment $\geq$19.5 months post-registration maintaining a partial tumor response. Five patients demonstrated stable disease for more than 6 months (1 pt at 500 µg; 750 µg; 1.5 mg; 1.75 mg and 2.0 mg doses) prior to disease progression. PFS and OS are presented by dose level in Table 2.

TABLE 2

Clinical outcomes

| Dose level | median number of cycles (range) | immune response | Individual patient PFS in months | Individual patient OS in months |
|---|---|---|---|---|
| 500 µg (n = 5) | 4 (2-6) | unknown | 1.4, 4.8, 4.9 | 7.8, 19.3, 20.6 |
| | | no | 4.5 | 14.9 |
| | | yes | 8.3 | 48.9 |
| 750 µg (n = 5) | 4 (1-9) | no | 1.1, 1.9, 3.7, 15.8 | 3.4, 4.0, 7.2, 51.2+ |
| | | yes | 4.6 | 24.7 |
| 1.0 mg (n = 5) | 1 (1-2) | unknown | 0.9 | 2.1 |
| | | no | 1.0, 1.0, 1.1, 1.8 | 6.3, 7.5, 9.9, 18.9 |
| 1.25 mg (n = 5) | 1 (1-3) | unknown | 0.9, 0.9, 1.0 | 1.4, 3.1, 5.3 |
| | | no | 2.7, 2.8 | 7.6, 17.4 |
| 1.5 mg | 4 | no | 2.8 | 7.2 |

TABLE 2-continued

Clinical outcomes

| Dose level | median number of cycles (range) | immune response | Individual patient PFS in months | Individual patient OS in months |
|---|---|---|---|---|
| (n = 3) | (3-7) | yes | 4.2, 10.3 | 6.2, 24.0 |
| 1.75 mg | 2 | unknown | 1.0 | 18.6 |
| (n = 5) | (1-6) | no | 1.1, 1.9, 2.1, 8.2 | 2.7, 3.2, 10.4, 27.2+ |
| 2.0 mg | 4 | unknown | 0.7 | 7.2 |
| (n = 6) | (1-12+) | no | 1.1, 4.8, 5.6, 8.3, | 7.5, 14.1+, 16.8+, 17.9+ |
|  |  | yes | 19.5+ | 22.2+ |

* bold faced numbers indicate patients who had a 2-4 fold increase in at least one tetramer positive CTL Post-treatment tetramer data were not available for 9 patients due to progression during the first 4 weeks of treatment (6 patients), adverse reaction on day 1 (1 patient), or failure to submit post-treatment blood specimens (2 patients). Of the 13 patients with tetramer data among the 20 patients enrolled on the 1.25 mg dose or lower, none of 4 patients that were tetramer positive to at least one melanoma specific peptide prior to treatment developed a immune response and 2 of 9 patients tetramer negative to the melanoma specific peptides prior to treatment developed an immune response to gp100. Of the 12 patients with tetramer data among the 14 patients enrolled at the 1.5 mg dose and higher, all 12 patients were tetramer positive to at least one melanoma specific peptide prior to treatment but the 3 patients who developed an immune response did so against peptides they were tetramer negative prior to treatment (gp 100: 2 patients; tyrosinase: 1 patient). In addition, 1 of 4 patients at the 1.75 mg and 4 of 5 at the 2.0 mg dose had 2-4 fold increases in at least one melanoma specific tetramer positive CTL (Mart-1: 1 patient; gp100: 4 patients; tyrosinase: 2 patients).

There were immune cell subset immunophenotyping data for 22 of the 34 eligible patients. Two-fold or more increases from pre-treatment levels were most often seen in CD3/CD69 expressing activated T cells (6/22). Dendritic cell analysis revealed an increase in the frequency (at least doubling) of the following cell subsets: CD40/DR (6/22); CD11c/CD80 (5/22); CD11c/CD83 (7/22); and CD11c/CD86 (6/22).

All patients have been followed to death or a minimum of 14 months. The reasons patients discontinued study treatment included tumor progression (31 patients) and grade 4 dyspnea (2 patients). At last contact, 1 patient was alive without disease, progression, 5 were alive with disease progression, and 28 were deceased due to disease progression. PFS and OS are presented by dose level in Table 2.

With regard to changes in immune (tetramer) response and associated clinical benefit of therapy, progression-free survival ranged from 4 to 19.5+ months (median: 8.4 months) among the 5 patients who developed an immune response; 1-15.8 months (median: 2 months) in the 20 patients who did not develop an immune response; and 1-4.6 months (median: 1 month) among the 9 patients who did not have immune data (Table 2)

Overall, these results demonstrate that aero-GMCSF therapy administered at up to 2 mg/dose can be safe and can correlate with increased frequencies of tumor specific CTLs in a dose-dependent fashion. In particular, an increased frequency of tetramer positive CTLs against gp100 was observed. For example, three of 16 patients that were tetramer positive for some melanoma differentiation antigens (e.g. MART-1) prior to treatment developed an immune response (IR) to new differentiation antigens (e.g. gp100) after therapy, and two of 9 patients who were tetramer negative to all melanoma differentiation antigens prior to treatment developed an IR against gp100.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating metastatic cancer of the lung in a human, said method comprising administering, to said lung of said human, between 2.0 and 8 mg of a granulocyte-macrophage colony stimulating factor in a 24 hour period.

2. The method of claim 1, wherein said granulocyte-macrophage colony stimulating factor is administered in the form of an aerosol.

3. The method of claim 1, wherein said granulocyte-macrophage colony stimulating factor is administered twice daily to said human.

4. The method of claim 1, wherein between 750 µg and 5 mg of said granulocyte-macrophage colony stimulating factor is administered in a 12 hour period.

5. The method of claim 1, wherein said granulocyte-macrophage colony stimulating factor is administered for seven days, followed by seven days of no administration of said granulocyte-macrophage colony stimulating factor.

6. The method of claim 1, wherein between 750 µg and 5 mg of said granulocyte-macrophage colony stimulating factor is administered per dose.

7. The method of claim 6, wherein between 1 mg and 2.5 mg of said granulocyte-macrophage colony stimulating factor is administered per dose.

8. The method of claim 7, wherein 2 mg of said granulocyte-macrophage colony stimulating factor is administered per dose.

9. The method of claim 1, wherein said metastatic cancer of the lung is a renal cell carcinoma, leiomyosarcoma, Ewing's sarcoma, osteosarcoma, or melanoma.

* * * * *

UNITED STATES PATENT AND TRADEMARK OFFICE
CERTIFICATE OF CORRECTION

| | |
|---|---|
| PATENT NO. | : 8,530,428 B2 |
| APPLICATION NO. | : 12/529897 |
| DATED | : September 10, 2013 |
| INVENTOR(S) | : Markovic |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 774 days.

Signed and Sealed this
Twenty-fourth Day of February, 2015

Michelle K. Lee
*Deputy Director of the United States Patent and Trademark Office*